(12) United States Patent
Shimizu et al.

(10) Patent No.: US 6,716,610 B2
(45) Date of Patent: Apr. 6, 2004

(54) ESTERIFICATION OR HYDROLYSIS WITH SUBSTRATE TREATED UN-DRIED IMMOBILIZED LIPOLYTIC ENZYME

(75) Inventors: Masami Shimizu, Ibaraki (JP); Toshiteru Komatsu, Ibaraki (JP); Masao Shimizu, Ibaraki (JP); Minoru Kase, Ibaraki (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/453,078

(22) Filed: Dec. 2, 1999

(65) Prior Publication Data

US 2003/0096383 A1 May 22, 2003

(30) Foreign Application Priority Data

Dec. 7, 1998 (JP) ............................. 10-346822
Dec. 10, 1998 (JP) ............................. 10-350920

(51) Int. Cl.$^7$ .............................. C12P 7/64; C12P 7/62; C12N 11/08
(52) U.S. Cl. .................. 435/134; 435/135; 435/180
(58) Field of Search ................. 435/134, 174, 435/180

(56) References Cited

U.S. PATENT DOCUMENTS

| 5,128,251 A | * | 7/1992 | Yokomichi et al. | ......... 435/134 |
| 5,177,013 A | | 1/1993 | Usui et al. | .................. 435/176 |
| 5,292,649 A | * | 3/1994 | Kosugi et al. | .............. 435/136 |
| 6,258,575 B1 | | 7/2001 | Shimizu et al. | ............. 435/134 |
| 6,337,414 B1 | * | 1/2002 | Sugiura et al. | ............. 554/174 |

FOREIGN PATENT DOCUMENTS

| EP | 0 320 132 A2 A3 | 6/1989 |
| JP | 62-134090 | 6/1987 |
| JP | 9-257 | 1/1997 |

OTHER PUBLICATIONS

Balcao Victor M. et al., "Bioreactors with immobilized lipases: State of the art." Enzyme and Microbial Technology, vol. 18, No. 6, 1996, pp. 392–416.

Villeneuve Pierre et al., "Customizing lipases for biocatalysis: A survey of chemical, physical and molecular biological approaches." Journal of Molecular Catalysis B Enzymatic, vol. 9, No. 4–6, Apr. 21, 2000, pp. 113–148.

\* cited by examiner

*Primary Examiner*—David M. Naff
(74) *Attorney, Agent, or Firm*—Oblon, Spivak, McClelland, Maier & Neustadt, P.C.

(57) ABSTRACT

A lipolytic enzyme such as lipase is adsorbed on a porous anion-exchange resin carrier to obtain an immobilized enzyme without drying. The un-dried immobilized enzyme is contacted with a fat or oil for a time which may be about 2 hours to about 24 hours to stabilize the immobilized enzyme, and the immobilized enzyme is recovered from the fat or oil. The recovered immobilized enzyme is then used for esterifying or hydrolyzing a substrate. Water content of the un-dried immobilized enzyme may be 20% or more be weight such as 20–60%. Prior to immobilization, the resin carrier may be treated with a lypophylic aliphatic acid which preferably has 8 to 18 carbons.

8 Claims, No Drawings

ESTERIFICATION OR HYDROLYSIS WITH SUBSTRATE TREATED UN-DRIED IMMOBILIZED LIPOLYTIC ENZYME

TECHNICAL FIELD

The present invention relates to a process for preparing an immobilized enzyme showing a high activity with a less loss in the enzyme activity, which is used for hydrolysis of fats and oils, ester-exchange of fats and oils, and esterification of aliphatic acids and alcohols. The term of "fats and oils" means an inclusion of a fat, an oil, a lard, a grease and so on.

BACKGROUND ART

In hydrolyzing fats and oils by a lipolytic (or fat and/or oil-decomposing) enzyme, an immobilized enzyme prepared by immobilizing a lipolytic enzyme onto an inorganic or organic carrier is used for efficient use of the enzyme. To raise the absorptivity of the enzyme onto a carrier and to improve an enzyme activity, various studies have been made, and for example, JP-A 9-257 discloses a process for producing an immobilized enzyme carrier prepared by immobilizing a lipase onto an inorganic carrier treated with a silane coupling agent having a special functional group, washing and drying it, and impregnating it with an aliphatic acid. Even by this method, however, the amount of the adsorbed enzyme and the enzyme activity remain still insufficient.

Further, an immobilized enzyme prepared by immobilizing a lipolytic enzyme called lipase onto a carrier is used as an enzyme mainly for use in reactions for the object of ester-exchanging (ester-interchanging or transesterifying) fats and oils and esterifying aliphatic acids and alcohols. These reactions are advantageously conducted at concentrations of water as low as possible (1000 ppm or less) to inhibit hydrolysis, and thus the immobilized enzyme is forcibly dried to give only several % water content in the carrier, since the immobilized enzyme is prepared.

However, the adsorbed enzyme tends to inactivate in the step of drying the immobilized enzyme, and there are many cases where the enzyme does not exhibit the maximum activity upon adsorption and when the enzyme exhibits activity thereof actually.

JP-A 62-134090 describes that after immobilization, the immobilized enzyme is dried under contact with aliphatic acid derivatives thereby raising its activity expression, but this method is neither practical nor efficient because expensive facilities are necessary for drying the immobilized enzyme and furthermore it is complicated to set up conditions etc. for slow drying.

Under these circumstances, it is desired that a lipolytic enzyme is prepared so as to exhibit its activity expression sufficiently and to prevent the enzyme from being left (or removed) or inactivated, whereby the amount of the enzyme used for lipolysis is reduced and the esterification reaction is promoted.

DISCLOSURE OF THE INVENTION

To solve this problem, it is desirable that a larger amount of a lipolytic enzyme is adsorbed at adsorption step so as to express high activity and that an atmosphere for promoting the reaction is created around the immobilized enzyme. The present invention relates to a process for preparing an immobilized enzyme for a lipolysis (or decomposition of fats and oils), which comprises absorbing and immobilizing the enzyme onto a porous, anion-exchanging resin as an immobilizing carrier, and which is treated with fats and oils, and the problem described above was thereby solved.

As a result of eager study by the present inventors to solve this problem, they found that it is necessary to confer a stable state on the enzyme adsorbed onto the carrier, for which it is effective to bring a reaction substrate. (or reactant) into contact with the enzyme rapidly after immobilization.

That is, the present invention relates to a process for esterification reaction, which comprises immobilizing a lipolytic enzyme on a carrier for immobilization by adsorption and, without drying, directly bringing the immobilized enzyme into contact with its substrate.

That is, in the present invention, the lipolytic enzyme in a un-dried state after immobilization is brought into contact with its substrate there by providing the immobilized enzyme with a higher degree of adsorption and a higher activity.

The invention provides a process for preparing an immobilized enzyme, which comprises the steps of:
  immobilizing a lipolytic enzyme on a porous, anion-exchanging resin for a carrier by adsorption and,
  without drying, treating the immobilized enzyme with fats and oils or a derivative of fats and oils.

The process may preferably further comprise the step of treating the carrier's resin with a lypophylic (or fat and/or oil-solving) aliphatic acid or a derivative of a lypophylic aliphatic acid in advance to the immobilization step.

The immobilized enzyme may be treated with fats and oils and the obtained immobilized enzyme is usable for hydrolysis.

Alternatively the immobilized enzyme may be treated with the derivative of fats and oils and the obtained immobilized enzyme is usable for esterification.

The used enzyme is preferably lipase.

The invention provides also use of the immobilized enzyme as defined above for hydrolysis or esterification of fats and oils or a derivative of fats and oils, for example hydrolysis of fats and oils, esterification of derivatives of fats and oils such as partial glycerides, glycerol and an aliphatic acid.

In addition, the invention provides a process for esterifying reaction substrates, which comprises the steps of:
  immobilizing a lipolytic enzyme on a porous, anion-exchanging resin for a carrier by adsorption and,
  without drying, bringing the immobilized enzyme into contact with the reaction substrates.

The invention moreover provides a process for hydrolysis of reaction substrates, which comprises the steps of:
  immobilizing a lipolytic enzyme on a porous, anion-exchanging resin for a carrier by adsorption and,
  without drying, treating the immobilized enzyme with reaction substrates and
  hydrolyzing the reaction substrates.

In esterification and hydrolysis, the reaction substrates may be fats and oils, such as triglycerides, or a derivative of fats and oils. The derivative of fats and oils may be an aliphatic acid, glycerol or partial glycerides such as monoglycerides and diglycerides.

According to the invention, the immobilized enzyme can be treated with the reaction substrates for hydrolysis or esterification, immediately being subject to the reaction. Alternatively, the immobilized enzyme can be stored after treatment with fats and oils or a derivative of fats and oils.

MODES FOR CARRYING OUT THE INVENTION

The carrier used in the present invention is preferably a porous, anion-exchanging resin. The particle diameter of the resin is desirably 400 to 1000 μm, and the diameter of its pore is desirably 100 to 1500 Å.

The resin materials include phenol formaldehyde based, polystyrene based, acrylamide based, divinyl benzene based. In particular, phenol formaldehyde-based resin (e.g. tradename: Duolite A-568) is desirable. Its pores give a large surface area for adsorption of the enzyme to obtain a larger amount for adsorption.

In the present invention, the carrier is treated preferably with a lypophylic aliphatic acid or a lypophylic aliphatic acid derivative for pre-treatment before immobilization, thus creating a state of adsorption to exhibit a high activity. The lypophylic aliphatic acid or lypophylic aliphatic acid derivative used has preferably 8 to 18 carbon atoms. For example, said aliphatic acid includes linear and saturated aliphatic acids such as capric acid, lauric acid and myristic acid, unsaturated aliphatic acids such as oleic acid and linoleic acid, hydroxy aliphatic acids such as ricinoleic acid, or branched aliphatic acids such as isostearic acid. The aliphatic acid derivative includes esters between $C_8$ to $C_{18}$ aliphatic acids and compounds having a hydroxyl group, and examples thereof include mono-alcohol monohydric alcohol or monovalent alcohol) esters, polyhydric alcohol polyol or polyvalent alcohol) esters, phospholipids, or derivatives of these esters to which ethylene oxide has been added. The mono-alcohol esters include methyl ester, ethyl ester, and the polyvalent alcohol esters include monoglyceride, diglyceride and derivatives thereof, or polyglycerol fatty acid esters, sorbitan fatty acid esters, sucrose fatty esters.

It is desirable for the process that any of these aliphatic acids and derivatives thereof is in the state of liquid at ordinary temperatures. These may be used alone, or these are combined to bring about further effects. It is considered that these derivatives are chemically decomposed in an aqueous catalyst or hydrolyzed with a lipolytic enzyme, to form aliphatic acids.

To bring these lypophylic aliphatic acids and derivatives thereof into contact with the porous anion-exchange resin, they may be added directly as such to water or an organic solvent, or to improve dispersibility, the lypophylic aliphatic acids or derivatives thereof are once dispersed and dissolved in a solvent and then they may be added to the porous anion-exchange resin dispersed in water. The organic solvent used in this step includes chloroform, hexane, ethanol. The ratio of the lypophylic aliphatic acid or the derivative thereof to the porous anion-exchange resin is preferable to be 0.01 to 1 part by weight, and particularly preferable to be 0.05 to 0.5 part by weight, of the lypophylic aliphatic acid or the derivative thereof as compared with 1 part (dry weight basis) by weight of the porous, anion exchange resin. The temperature for contact is 0 to 100° C., preferably 20 to 60° C. The time for contact may be about 5 minutes to about 5 hours. After this treatment, the resin is recovered by filtration and then may be dried at this time. The temperature for drying is preferably room temperature to 100° C., and drying under reduced pressure may be conducted.

The lipolytic enzyme used in the present invention includes lipases derived (or originated) from microorganisms (microbes or germs) of the genera Rizopus, Aspergillus, Chromobacterium, Mucor, Pseudomonas, Geotrichum, Penicillium and Candida as well as animal lipases such as pancreatic lipase. To obtain aliphatic acids at high degrees of decomposition or to obtain triglycerides at high degrees of esterification, a lipase (random type) having no position selectivity is preferable, and the enzyme derived from the microorganism is preferably selected from the genera Pseudomonas and Candida.

To obtain a partial glyceride such as monoglyceride and diglyceride at high degrees of esterification, a lipase having position selectivity is preferable.

The temperature for conducting an immobilization is well 0 to 60° C., preferably 5 to 40° C., because of no arising inactivation of an enzyme, but the temperature can be selected depending on the characteristics of the enzyme used. The pH of the enzyme solution is well in the range as far as the enzyme is not denatured. The pH 3 to 9 is desirable. The pH can also be determined similarly to the temperature, depending on the characteristics of the enzyme. The buffer for maintaining the pH includes, but is not limited to, acetic acid-based buffer, phosphoric acid-based buffer and Tris-HCl-based buffer.

In the method of immobilization according to the present invention, the concentration of the enzyme in the enzyme solution is desirable to be the solubility of the enzyme or below and to be sufficient concentration, in respect of immobilization efficiency. If necessary, insoluble enzymes were removed by centrifugation, and then a supernatant can be used. The ratio of the enzyme to the carrier for immobilization is preferable to be 0.05 to 10 part by weight, and particularly preferable to be 0.1 to 5 part by weight, of the enzyme as compared with 1 part by weight of the carrier for immobilization.

To bring the enzyme into contact with the carrier treated as described above, it is possible to use a method of dispersing and stirring a carrier in an enzyme solution or a method of introducing a carrier into a packing tower (or packing column) such as column etc. and circulating an enzyme solution through it using a pump and so on. Any method thereof may be used.

The process up to this step in preparation of the immobilized enzyme for hydrolysis of fats and oils may be the same as in preparation of the immobilized enzyme for esterification reaction.

Hereinafter, preferable embodiments for preparing the immobilized enzyme for hydrolysis of fats and oils are described.

The reaction substrate, which is used in the present invention and which is made to treat the immobilized enzyme after immobilization, includes the fats and oils such as rapeseed oil, soybean oil, corn oil, olive oil, tallow, fish oil. Although they are not limited, fats and oils actually hydrolyzed are desirably used.

To bring the substrate into contact with the immobilized enzyme after immobilization, the immobilized enzyme is recovered by filtration from the enzyme solution after immobilization, then excess water content is removed, and without drying, the immobilized enzyme is brought into contact with fats and oils as the substrate. The water content in the immobilized enzyme, though being varied depending on the type of carriers used, is 20% or more by weight and preferably in the range of 40 to 60% by weight. The immobilized enzyme may be introduced into a packing vessel such as column to circulate fats and oils through the packing vessel with e.g. a pump, or the immobilized enzyme may be dispersed in fats and oils. The temperature for contact is preferable to be ordinary temperature to 60° C., and this temperature can be selected depending on the characteristics of the enzyme. Further, the time for contact may be about 2 hours to about 24 hours. After this contact is finished, it is filtered to recover the immobilized enzyme. By this operation, the reaction site of the immobilized enzyme is considered to become suitable for hydrolysis. The immobilized enzyme after subjected to this treatment is good in storage stability. This is considered due to the stabilization of lipase by fats and oils.

Hereinafter, preferable embodiments for preparing the immobilized enzyme for esterification reaction are described.

The substrate includes $C_2$ to $C_{22}$ aliphatic acids. These may be either saturated or unsaturated, or may contain a linear chain besides a branched chain and/or a conjugated double bond etc. Further, the substrate may contain structural isomers thereof and is not particularly limited. For preparation of esters having a single aliphatic acid component, partial glycerides and/or triglycerides, these aliphatic acids can be used alone or may be used as a mixture of two or more type thereof. Further, the aliphatic acids may be used as completely or partially decomposed from one or more vegetable oils and/or animal fats. On the other hand, the alcohols include $C_1$ to $C_{22}$ monohydric alcohols and dihydric or more-hydric alcohols. As the substrate, the aliphatic acids and alcohols described above are combined such that a desired esterified product can be produced, and the substrate is not limited to specific compounds.

The immobilized enzyme after immobilized by adsorption is deprived (or removed) of water sufficiently by a physical method and then brought into contact with the substrate to effect the esterification reaction. The water content in the immobilized enzyme, though being varied depending on the type of carriers used, is usually 20% or more by weight and preferably in the range of 40 to 60% by weight.

In the case of the esterification reaction, the reaction is conducted by shift under dehydration, and therefore, while the reaction is conducted, excess water content remaining in the immobilized enzyme can simultaneously be removed by use of a dehydration system. After the lipolytic enzyme is immobilized by adsorption onto a carrier for immobilization, the initial esterification reaction is conducted by directly bringing the immobilized enzyme without drying into contact with the substrate, and removal of this excess water content in this initial esterification reaction requires extra reaction time but can be effected in a considerably shorter time than the time for conventionally conducted drying of the immobilized enzyme. Further, the composition and qualities of a product produced in this initial reaction are in no way inferior to those of a product produced in the second or later reaction. In this initial esterification reaction, the time elapsed until a water content being enough for enzyme to exhibit its activity, though being varied depending on the amount of the immobilized enzyme and on the ability of the dehydration system used, is approximately 1 hour or so. Because excess water content was removed in the initial reaction, the time required for removal of water in the initial reaction is not necessary in the second or later reaction in which the immobilized enzyme for esterification reaction can be obtained.

For the method for esterification reaction, it is possible to use any methods known in the public art, such as dehydration under reduced pressure, glycerol dehydration, and dehydration using a dehydrating agent such as molecular sieves. Further, the immobilized enzyme maybe used in a stirring reactor, a packed column reactor and a fluidized bed reactor.

According to the present invention, the maximum activity of the adsorbed enzyme is brought about and the esterification reaction can be conducted efficiently and stably for a long period of time by conferring a stable state on the immobilized enzyme and by maximally preventing the enzyme from being inactivated due to drying.

EXAMPLES

Example 1

10 g Duolite A-568 (Diamond Shamrock Co., Ltd.) was stirred for 1 hour in 100 cc of 1/10 N NaOH. After filtration, it was washed with 100 cc of deionized water and the pH was equilibrated with 100 cc of 500 mM acetic acid-based buffer (pH 7). Thereafter, the pH was equilibrated twice for 2 hours with 100 cc of 50 mM acetic acid-based buffer (pH 7). Thereafter, the carrier was recovered by filtration and then 50 cc of ethanol was used to replace the solvent by ethanol for 30 minutes. After filtration, 50 cc of ethanol containing 10 g of ricinoleic acid was added and the ricinoleic acid was adsorbed onto the carrier for 30 minutes. Thereafter, the carrier was recovered by filtration and washed 4 times for 30 minutes with 50 cc of 50 mM acetic acid-based buffer (pH 7) to remove the ethanol, and the carrier was recovered by filtration. Thereafter, the carrier was brought into contact for 5 hours with an enzyme solution containing 10 g of commercial lipase (Lipase OF, Meito Sangyo Co., Ltd.) dissolved in 90 cc of 50 mM acetic acid-based buffer (pH 7) whereby the enzyme was immobilized on the carrier. The immobilized enzyme was recovered by filtration and washed with 100 cc of 50 mM acetic acid-based buffer (pH 7), to wash an enzyme and protein not being immobilized. Thereafter, 40 g of soybean oil to be actually decomposed was added thereto and stirred for 12 hours. All the above operations were conducted at 20° C. Thereafter, the immobilized enzyme was separated by filtration from the oil. The degree of immobilization as measured by the difference between the residual activity of the enzyme solution after immobilization and the activity of the enzyme solution before immobilization was 82%. This is about 20% higher than the degree of immobilization by the conventional method.

2.8 g (1 g on the dry weight basis) of the immobilized enzyme thus obtained was weighed precisely in 50 cc Erlenmeyer flask equipped with a screw. 10 g of soybean oil and 6 g of distilled water were added thereto and allowed to react at 40° C. under shaking at 200 rpm. 30 minutes after the reaction was initiated, the degree of decomposition was 83%. In the 2-hour reaction, the degree of decomposition reached 97%. As the degree of decomposition, a value obtained by dividing the acid value (AV) by the saponification value (SV) is expressed in percentage. This decomposition rate is the highest level among those of the immobilized enzyme prepared in methods reported heretofore.

Example 2

After the reaction was finished according to the method shown in Example 1, the total amount of the immobilized enzyme was recovered, and the reaction was repeated with the initial charged compositions shown in Example 1. The reaction was repeated 5 times, and for 2 hours after the reaction was initiated, the degrees of decomposition of 97.0%, 97.2%, 96.5%, 96.8% and 96.5% were obtained respectively.

Example 3

10 g Duolite A-568 (Diamond Shamrock Co., Ltd.) was stirred for 1 hour in 100 cc of 1/10 N NaOH. After filtration, it was washed with 100 cc of deionized water and the pH was equilibrated with 100 cc of 500 mM acetic acid-based buffer (pH 7). Thereafter, the pH was equilibrated twice for 2 hours with 100 cc of 50 mM acetate buffer (pH 7).

Thereafter, the carrier was recovered by filtration and then 50 cc ethanol was used to replace the solvent by ethanol for 30 minutes. After filtration, 50 cc of ethanol containing 10 g of ricinoleic acid was added and the ricinoleic acid was adsorbed onto the carrier for 30 minutes. Thereafter, the carrier was recovered by filtration and washed 4 times for 30 minutes with 50 cc of 50 mM acetic acid-based buffer (pH 5) to remove the ethanol, and the carrier was recovered by filtration. Thereafter, the carrier was brought into contact for 5 hours with an enzyme solution containing 10 g of commercial lipase (Li Lipase, Nagase Sangyo Co., Ltd.) dissolved in 90 cc of 50 mM acetic acid-based buffer (pH 7) whereby the enzyme was immobilized on the carrier. The immobilized enzyme was recovered by filtration and washed with 100 cc of 50 mM acetic acid-based buffer (pH 7), to wash an enzyme and protein not being immobilized. All the above operations were conducted at 20° C. The degree of immobilization as measured by the difference between the residual activity of the enzyme solution after immobilization and the activity of the enzyme solution before immobilization was 98%.

Then, 100 g of aliphatic acid formed by decomposition of soybean oil was added and stirred well, and 16 g of glycerol was added, and the esterification reaction was conducted at 40° C. under reduced pressure (13 Pa or less).

The DG (diglyceride) yield (diglyceride content+ triglyceride content) in the reaction oil reached 63% in 4 hours of the reaction. After this reaction, the oil after the reaction was separated by filtration to recover the total amount of the immobilized enzyme, and 100 g of the above soybean-decomposed aliphatic acid and 16 g of glycerol were added thereto, and the same reaction was repeated further twice. As a result, the DG yield in the oil after the reaction was 62% in 2 hours of any reaction conducted twice. In the repeated reaction described above, the composition of components in the reaction oil upon the reaction at a DG yield of about 62% is shown in Table 1.

Comparative Example 1

The immobilized enzyme prepared in Example 3 was dried at 40° C. under reduced pressure (133 Pa or less) for a whole day and night in the absence of the soybean oil-decomposed aliphatic acid shown in Example 3. The water content in the immobilized enzyme after drying was about 2%. Using 10 g of this immobilized enzyme, the esterification reaction was repeated 3 times in the same manner as in Example 3. As a result, the DG yield in any reaction was 62 to 63% in 3 hours of the reaction. In the repeated reaction described above, the composition of components in the reaction oil upon the reaction at a DG yield of about 62% is shown in Table 1.

TABLE 1

| | | Reaction time (hr) | Proportion of component (% by weight) | | | | | Yield (%) | Purity (%) |
|---|---|---|---|---|---|---|---|---|---|
| | | | FA | GLY | MG | DG | TG | DG + TG | DG/(DG + TG) |
| Example | 1st time | 4 | 20.5 | 0.5 | 16.0 | 60.0 | 3.0 | 63.0 | 95.2 |
| | 2nd time | 2 | 17.6 | 0.8 | 19.8 | 59.0 | 2.8 | 61.8 | 95.4 |
| | 3rd time | 2 | 17.6 | 0.8 | 20.0 | 59.0 | 2.6 | 61.6 | 95.7 |
| Comparative example | 1st time | 3 | 18.9 | 0.7 | 18.5 | 59.6 | 2.3 | 61.9 | 96.3 |
| | 2nd time | 3 | 17.2 | 0.7 | 19.1 | 60.2 | 2.8 | 63.0 | 95.6 |
| | 3rd time | 3 | 17.2 | 0.8 | 19.0 | 58.5 | 4.5 | 63.0 | 92.9 |

FA; fatty acid
GLY; glycerol
MG; monoglyceride
DG; diglyceride
TG; triglyceride

The proportion of components in the oil after the reaction in the Examples above is a result obtained by analyzing the sample with gas chromatography after trimethylsilylation.

Comparison between Example 3 and Comparative Example 1 above revealed that when the reaction was conducted without drying the immobilized enzyme according to the method of the present invention, the reaction time can be reduced while the qualities of the product are not deteriorated. Comparison between the esterification activities of the respective enzymes indicates that the enzyme treated with the reaction substrate exhibited 150% activity (as compared with the dried enzyme).

What is claimed is:

1. A process for esterifying reaction substrates which use an immobilized lipolytic enzyme which comprises:
   i) immobilizing a lipolytic enzyme on a porous, anion-exchanging resin carrier by adsorption to provide an immobilized lipolytic enzyme having a water content of 20 to 60% by weight, without drying the immobilized lipolytic enzyme;
   ii) treating the immobilized lipolytic enzyme formed in step i) by contacting the immobilized lipolytic enzyme containing 20 to 60% by weight of water with fats or oils or a derivative of fats or oils;
   iii) separating the treated immobilized lipolytic enzyme from the fats or oils in step ii); and
   iv) esterifying said reaction substrate by contacting the separated immobilized lipolytic enzyme from step iii) with said reaction substrate.

2. The process as claimed in claim 1, wherein said resin carrier is treated with a lypophylic aliphatic acid or a derivative of a lypophylic aliphatic acid in advance of said immobilization step.

3. The process as claimed in claim 1, wherein said lipolytic enzyme is a lipase.

4. The process as claimed in claim 1, wherein said reaction substrate is a fat or oil.

5. A process for hydrolyzing reaction substrates which use an immobilized lipolytic enzyme which comprises:
   i) immobilizing a lipolytic enzyme on a porous, anion-exchanging resin carrier by adsorption to provide an immobilized lipolytic enzyme having a water content of 20 to 60% by weight, without drying the immobilized lipolytic enzyme;

ii) treating the immobilized lipolytic enzyme formed in step i) by contacting the immobilized lipolytic enzyme containing 20 to 60% by weight of water with fats or oils or a derivative of fats or oils;

iii) separating the treated immobilized lipolytic enzyme from the fats or oils in step ii); and iv) hydrolyzing said reaction substrate by contacting the separated immobilized lipolytic enzyme from step iii) with said reaction substrate.

6. The process as claimed in claim 5, wherein said resin carrier is treated with a lypophylic aliphatic acid or a derivative of a lypophylic aliphatic acid in advance of said immobilization step.

7. The process as claimed in claim 5, in which the enzyme is lipase.

8. The process as claimed in claim 5 herein said reaction substrate is a fat or oil.

* * * * *